US006420165B1

(12) United States Patent
Weinstein et al.

(10) Patent No.: US 6,420,165 B1
(45) Date of Patent: *Jul. 16, 2002

(54) DEGRADING SLUDGE WITH MICROORGANISMS ATCC 55926 OR 202050

(75) Inventors: Bernard I. Weinstein, Engelwood; David Figurski, Dumont, both of NJ (US); Sadayori Hoshina, Tokyo (JP); Koji Nakanishi, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/577,640

(22) Filed: May 24, 2000

Related U.S. Application Data (63) Continuation of application No. PCT/US98/24924, filed on Nov. 25, 1998, which is a continuation-in-part of application No. 08/979,586, filed on Nov. 26, 1997, now Pat. No. 6,190,903.

(51) Int. Cl.[7] .............................. B09B 3/00; C12N 1/00; C12N 1/02; C12N 1/20; D06M 16/00
(52) U.S. Cl. ............................... 435/262.5; 435/252.5; 435/261; 435/264; 435/832
(58) Field of Search .............................. 435/243, 252.1, 435/822, 262.5, 261, 264, 832

(56) References Cited

U.S. PATENT DOCUMENTS

| 5,610,061 A | 3/1997 | Pierce et al. ............. 435/252.1 |
| 5,736,032 A | 4/1998 | Cox et al. ................... 424/76.5 |
| 5,783,431 A | 7/1998 | Peterson et al. ......... 435/172.3 |
| 6,190,903 B1 * | 2/2001 | Weinstein et al. ....... 435/252.5 |

OTHER PUBLICATIONS

Cabirol, N., et al., (1996) "Role of Methanogenic and Sulfate–Reducing Bacteria in the Reductive Dechlorination of Tetrachloroethylene in Mixed Culture." Bull Environ Contam Toxicol 56: 817–824.

Deshusses, Marc, A., (1997) "Biological Waste Ait Treatment in Biofilters." Biotechnology 8 (3):335–339.

Gisi, D., Stucki, G., Hanselmann, W., (1997) "Biodegradation of the Pesticide 4, 6–dinitro–ortho–cresol by Microorganisms in Batch Cultures and in Fixed–bed Column Reactors." Appl Microbiol Biotechnol 48:441–448.

* cited by examiner

*Primary Examiner*—David M. Naff
*Assistant Examiner*—Deborah K. Ware
(74) *Attorney, Agent, or Firm*—John P. White; Cooper & Dunham LLP (57) ABSTRACT

A biologically pure culture of a microorganism is provided designated SH2A and deposited under ATCC Accession No. 55926, or a mutant derived therefrom. Further provided is a biologically pure culture of a microorganism designated SH2B and deposited under ATCC Accession No. 202050, or a mutant derived therefrom. A method of degrading an organic material such as sludge is carried out by treating the organic material with an effective, degrading amount of either SH2A or a mutant derived therefrom, or SH2B or a mutant derived therefrom. The microorganism designated SH2A or a mutant derived therefrom, or SH2B or a mutant derived therefrom, is grown by culturing the microorganism at a temperature and in a medium effective to promote growth of the microorganism.

12 Claims, 7 Drawing Sheets

Fig. 1

Sequence of 16S rRNA

GCGACGTTGTCCGGAATTATTGGGCGTAAAGCGCGCG
AGGCGGTCCTTTAAGTCTGATGTGAAAGCCCACGGCTC
AACCGTGGAGGGTCATTGGAAACTGGGGACTTGAGTG
CAGGAGAGGAGAGCGGAATTCCACGTGTAGCGGTGAAA
TGCGTAGAGATGTGGAGGAACACCAGTGGCGAAGGCGG
CTCTCTGGCCTGTAACTGACGCTGAGGCGCGAAAGCGT
GGGGAGCAAACAGGATTAGATACCCTGGTAGTCCACGC
CGTAAACGATGAGTGCTAAGTGTTAGAGGGGTCACACC
CTTTAGTGCTGTAGCTAACGCGATAAGCACTCCGCCTG
GGGAGTACGGCCGCAAGGCTGAAACTCAAAGGAATTGA
CGGGGGCCCGCACAAGCGGTGGAGCATGTGGTTTAATT
CGAAGCAACGCGAAGAACCTTACCAGGTCTTGACATCC
CCTGACAACCCAAGAGATTGGGCGTTCCCCTTCCGGG
GGACAAGGTGACACGTGGTGCATGGTTGTCTTCACCTC
GTTCTT

FIG. 3A
MICROORGANISM DEGRADATION IN SLUDGE

FREEZE/THAW

FIG. 3B

① Sludge is placed in the Freezing Container

Freezing Container
$\begin{cases} 2cm \times 25cm \times 25cm \\ 1cm \times 25cm \times 25cm \end{cases}$ ② Container is placed in the Cold Water Bath

Cold Water Bath with coolant (ADVANTEC LP-3300)

③ Frozen at -10°C for 3 hours

Antifreeze/Coolant (Niveline)

④ Thaw out with hot water. Poured into the beaker

FIG. 4A VACUUM FILTRATION

(1) Pour 20 ml sludge into Buchnar's (2) Vacuum Pump is activated, and Stopwatch is started

(3) The amount of filtered liquid dripping into the test tube and the time it takes is recorded (filtration velocity calculation)

FIG. 4B * For pressurized filtration, additional layer of filtration paper was placed on top of the sludge and 200 ml beaker filled with 200 ml of water was placed on top as weight

SEQUENCE LISTING

<160> NUMBER OF SEQ ID NOS: 3

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence:primer/probe

<400> SEQUENCE: 1
cagcagccgc ggtaatac                                                   18

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence:primer/probe

<400> SEQUENCE: 2
gattagatac cctggta                                                    17

<210> SEQ ID NO 3
<211> LENGTH: 538
<212> TYPE: DNA
<213> ORGANISM: Bacillus midousuji

<400> SEQUENCE: 3
gcgacgttgt ccggaattat tgggcgtaaa gcgcgcgcag gcggtccttt aagtctgatg      60
tgaaagccca cggctcaacc gtggagggtc attggaaact gggggacttg agtgcaggag     120
aggagagcgg aattccacgt gtagcggtga aatgcgtaga gatgtggagg aacaccagtg     180
gcgaaggcgg ctctctggcc tgtaactgac gctgaggcgc gaaagcgtgg ggagcaaaca     240
ggattagata ccctggtagt ccacgccgta aacgatgagt gctaagtgtt agagggtca     300 caccctttag tgctgtagct aacgcgataa gcactccgcc tggggagtac ggccgcaagg     360
ctgaaactca aaggaattga cgggggcccg cacaagcggt ggagcatgtg gtttaattcg     420
aagcaacgcg aagaacctta ccaggtcttg acatcccctg acaacccaag agattgggcg     480 ttccccttc cggggacaa ggtgacacgt ggtgcatggt tgtcttcacc tcgttctt       538

DEGRADING SLUDGE WITH MICROORGANISMS ATCC 55926 OR 202050

This application is a continuation of PCT International Application No. PCT/US98/24924, filed Nov. 25, 1988, designating the United States of America, which is a continuation-in-part of and claims priority of U.S. Ser. No. 08/979,586, filed Nov. 26, 1997, now U.S. Pat. No. 6,190,903 issued Feb. 20, 2001 the contents of which are hereby incorporated by reference into the present application.

Throughout this invention, various publications are referenced. The disclosure of these publications is hereby incorporated by reference into this application to describe more fully the art to which this invention pertains.

BACKGROUND

Human industrial activities inevitably generate industrial wastes. These industrial wastes primarily consist of inorganic and organic waste discharged by factories, agriculture, fisheries and food processing industries. The high cost of degrading or handling these wastes are borne by these industries. These costs hinder market expansion for these and other related businesses.

Currently, organic waste fermentation and treatment systems have been developed for utilizing waste. Using these systems, one can currently produce biologically active substances such as soil improvement agents, and compost.

It would be useful to manufacture and market a biomass fermentation and treatment method capable of converting wastes produced by fisheries, and vegetable and animals bioprocessing industries into biologically responsive modifiers, animal feed, fertilizer or fermentation agents. Such a method would include a system for treating waste and a new fermentation agent that would be useful in waste decomposition. Using such a system, one would be able to 1) reduce waste treatment costs, 2)prevent pollution of the environment, 3)improve soil, e.g. farmlands, and 4) yield biologically active reusable substances.

Accordingly, applicants sought a new bacterium capable of degrading lipids, proteins, carbohydrates, and wood fiber. Such a bacterium could be useful for many different purposes in biodegradation of waste. This new system of biodegradation would be capable of targeting different types of waste and broadening the applicability of waste degradative methods.

Applicants concentrated on thermophilic bacteria due to their rapid growth. Also, thermophilic bacteria are considered by many in the field to be the safest and most effective bacterium for use in bioprocessing procedures.

Thermophilic bacteria are an ideal choice for the following reasons because they are:
1) well studied/characterized;
2) aerobic;
3) capable of being manipulated for recombinant DNA purposes;
4) able to grow at a specific optimum high temperatures;
5) capable of stably maintaining introduced foreign genes; and
6) efficient and predictable expression of introduced exogenous genes to produce exogenous proteins.

SUMMARY OF THE INVENTION

This invention provides a biologically pure culture of a microorganism designated SH2A and deposited under ATCC Accession No. 55926, or a mutant derived therefrom.

This invention further provides a biologically pure culture of a microorganism designated SH2B and deposited under ATCC Accession No. 202050, or a mutant derived therefrom.

This invention provides a method of degrading an organic material which comprises treating the organic material with an effective, degrading amount of a microorganism designated SH2A and deposited under ATCC Accession No. 55926, or a mutant derived therefrom which retains the degrading activity thereof, so as to thereby degrade the material.

This invention further provides a method of degrading an organic material which comprises treating the organic material with an effective, degrading amount of a microorganism designated SH2B and deposited under ATCC Accession No. 202050, or a mutant derived therefrom which retains the degrading activity thereof, so as to thereby degrade the material.

This invention also provides a method for growing a microorganism designated SH2A and deposited under ATCC Accession No. 55926, or a mutant derived therefrom, which comprises culturing the microorganism at a temperature and medium effective to promote growth of the microorganism.

This invention also provides a method for growing a microorganism designated SH2B and deposited under ATCC Accession No. 202050, or a mutant derived therefrom, which comprises culturing the microorganism at a temperature and medium effective to promote growth of the microorganism.

DETAILED DESCRIPTION OF THE INVENTION

Throughout this application, references to specific nucleotides are to nucleotides present on the coding strand of the nucleic acid. The following standard abbreviations are used throughout the specification to indicate specific nucleotides:

| | |
|---|---|
| C = cytosine | A = adenosine |
| T = thymidine | G = guanosine |

As used herein ⁂aerobic⁂ means pertaining to or requiring oxygen.

The present invention provides for a biologically pure culture of a microorganism designated SH2A and deposited under ATCC Accession No. 55926, or a mutant derived therefrom.

Bacterium strain, *Bacillus midousuji* SH2A was deposited on Jan. 21, 1997 with the American Type Culture Collection (ATCC), 12301 Parklawn Drive, Rockville, Md. 20852, U.S.A., under the provisions of the Budapest Treaty For The International Recognition Of The Deposit Of Microorganisms For The Purposes Of Patent Procedure. Bacterium strain SH2A has been accorded ATCC Accession Number 55926.

This invention further provides a biologically pure culture of a microorganism designated SH2B and deposited under ATCC Accession No. 202050, or a mutant derived therefrom.

Bacterium strain, *Bacillus midousuji* SH2B was deposited on Oct. 24, 1997 which the American Type Culture Collection (ATCC), 12301 Parklawn Drive, Rockville, Md. 20852, U.S.A., under the provisions of the Budapest Treaty For The International Recognition Of The Deposit Of Microorganisms For The Purposes Of Patent Procedure. Bacterium strain SH2B has been accorded ATCC Accession No. 202050.

This invention further provides a method of degrading an organic material which comprises treating the organic material with an effective, degrading amount of a microorganism designated SH2A and deposited under ATCC Accession No. 55926, or a mutant derived therefrom which retains the degrading activity thereof, so as to thereby degrade the material.

Determination of an effective, degrading amount of microorganism as described in the claimed invention is within the knowledge of one skilled in the art. Various methods exist in which one can determine the amounts of the bacteria required to effectively degrade the waste of interest.

This invention further provides a method of degrading an organic material which comprises treating the organic material with an effective, degrading amount of a microorganism designated SH2B and deposited under ATCC Accession No. 202050, or a mutant derived therefrom which retains the degrading activity thereof, so as to thereby degrade the material.

The organic material degraded by the bacterial strains above include, but should not be limited to, plastics, specifically polyethylene. In one specific embodiment, the polyethylene may be irradiated prior to treatment with the bacterial strains to facilitate the degradative process. Specifically, in such an embodiment, the polyethylene may be irradiated with ultra-violet light.

The organic material degraded by the bacterial strains above may also comprise a protein, specifically waste products of households and such industries as food-processing, agriculture, dairy or fisheries. Specific examples include, but are not limited to, wood pulp, paper products, shellfish, coffee bean dregs, tunafish heads, squids and other by-products of these industries. Further kitchen waste may also be degraded by these bacteria. Kitchen waste may include, but are not limited to, paper products, shellfish, coffee bean dregs, tunafish heads, squids and other by-products found in kitchen bins, trash dumps and other consumer-based waste.

This invention further provides wherein organic material comprising a sugar is degraded by the methods described above. Specifically such sugars include, but are not limited to, mannose, maltose, trehalose, fructose and raffinose. Many of these sugars may be found in kitchen wastes and are by-products of industries in food-processing and agriculture, e.g. fruits.

The organic material also includes amino acid-based compounds. These compounds may be proteins, polypeptides, peptides, naturally occurring or synthetic.

The organic material may also include a nucleic acid molecule, specifically deoxyribonucleic acid molecules. DNAse activity has been described in these bacterial strains.

The above-identified methods can be effected at a temperature from about 62° C. to about 100° C. Specifically, the optimal growth temperature of the bacterial strains has been about 62° C.; however, the bioprocessing may take place at higher temperature. One skilled in the art would be capable of determining the optimal temperature for degrading material using these bacterial strains.

The above-identified methods can be effected at a pH at about 5.0 to about 8.0, specifically the pH is at about 7.4.

Further, these bacterial strains can be used in the above-identified methods in an aerobic environment.

This invention also provides a method for treating sludge comprising administering to the sludge a microorganism designated SH2A, a microorganism designated SH2B, or a combination thereof. In an embodiment, the sludge is an organic sludge.

This invention further provides a method for growing a microorganism designated SH2A and deposited under ATCC Accession No. 55926, or a mutant derived therefrom, which comprises culturing the microorganism at a temperature and medium effective to promote growth of the microorganism.

This invention further provides a method for growing a microorganism designated SH2B and deposited under ATCC Accession No. 202050, or a mutant derived therefrom, which comprises culturing the microorganism at a temperature and medium effective to promote growth of the microorganism.

One can grow the bacterial strains at a temperature of about 62° C. to about 100° C., specifically the temperature is about 62° C.

One can grow the bacterial strains at a pH from about 5.0 to about 8.0, specifically where the pH is about 7.4.

As described above, medium are currently known that are effective in promoting growth of these microorganism. Those skilled in the art would know which mediums would be effective in promoting the growth of these microorganisms. In a specific embodiment, applicants used trypticase soy medium.

This invention is illustrated in the Experimental Details section which follows. These sections are set forth to aid in an understanding of the invention but are not intended to, and should not be construed to, limit in any way the invention as set forth in the claims which follow thereafter. First Series Of Experiments:

MATERIALS AND METHODS

Bacterial strains: Origin of the isolates.

Strains SH2A and Strain SH2B were isolate from a sample of compost collected in Osaka, Japan.

Culture methods and Media.

Regular aerobic techniques were used in all experiments. Strains SH2A and SH2B were cultured on trypticase soy medium (BBL) at 64° C.

Sporulation test.

Nutrient Agar (Oxoid, UK) was used to test for sporulation. The plate was inoculated with an overnight culture and then incubated at 64° C. for up to 5 days to determine the presence of spores.

The heat-resistance of the cultured cells was determined in trypticase soy broth. After overnight incubation at 60° C., 70° C., 80° C., and 90° C. respectively, the viability of the cells was monitored by subculturing on trypticase soy agar plates at 64° C.

Morphological characteristics.

Morphological properties were determined by phase-contrast microscopy, and scanning electron microscopy.

Analytical techniques.

Aerobiosis was achieved by growing cultures in the Staphyogram Identification kit (Thermo, Japan). Acid production was tested in the presence of mannose, lactose, maltose, glycerol, salicin, trehalose, sucrose, mannitol, fructose and raffinose. Indole production was tested with Kovacs reagent. Nitrate reduction was tested with Griess's reagent. β-glucosidase, β-glucuronidase, argininedehydrase, and urease activity were also determined with the Staphyogram Identification kit. DNAase production was determined by the agar plate method using salmon sperm DNA and assessing halo formation after DNA precipitation with 1.5 N HCl. High salt tolerance by the cells was determined by growth of the bacterial culture in trypticase soy agar plates containing 7.5% NaCl at 64° C. overnight. Kanamycin and ampicillin resistance were measured by growing cells in Muller-Hinton agar plates containing 50 $\mu$g of each of these antibiotics at 64° C., overnight. Hemolysis was measured in trypticase soy agar plates containing 5% sheep blood at 64° C. overnight. Gram staining was performed using the standard method.

16S rRNA sequence studies.

Purification of genomic DNA, and amplification and purification of the 16S rRNA gene segment from isolate SH2A were performed using commercially available kits (Gene Amp kit, Geneclean spin). The purified PCR product was directly sequenced. Sequencing was performed on an ABI automated DNA sequencer using a Prism dideoxy terminating cycle sequence kit as recommended by the manufacturer (Applied Biosystems, LTD). The primers used for amplification and sequencing are 16SRR I: cag cag ccg cgg taa tac (Seq. I.D. No. I) and 16SRR VIII: gat tag ata ccc tgg ta (Seq. I.D. No. 2). The resulting DNA sequence for the 16S rRNA gene segment (DNA Strider) was aligned with 16S rRNA sequences obtained from the Ribosomal Database Project and from Genbank, and compared. The resulting DNA sequence for the 16S rRNA gene sequences was unique compared to known bacteria (FIG. 1) (Seq. I.D. No. 3).

Biodegradation of the tuna fish head and extraction of docosahexanoic acid (DHA).

One hundred kilogram of frozen tunafish heads (27% DHA) were mixed with a suspension of $1 \times 10^{11}$ cells of Strain SH2A and 10 g of vitamin E and incubated at 75° C., for 4 hours or 8 hours. The biodegraded samples were assayed for DHA. The saponified tunafish oil from each sample was assayed by treating the oil with 4N NaOH-ethylalcohol at 60° C. Free fatty acid was obtained by n-hexane extraction. Analysis of DHA in the fatty samples was performed using gas liquid chromatography (GLC).

Biodegradation of polychlorobiphenyl (PCB).

Trypticase soy broth containing twenty ppm of each isomeric PCB was inoculated with $1 \times 10^7$ cells/ml of the strain SH2B and was incubated at 64° C. up to 5 days. After incubation, the sample was extracted by n-hexane and analyzed by GLC.

Bacterial accumulation of heavy metal (Cd).

Six $\mu$g of Cd $(NO_3)4H_2O$ in trypticase soy broth (2.2 ppm of Cd) was mixed with $1 \times 10^7$ cells/ml of Strain SH2B and incubated at 64° C., for 3 days. After incubation, the sample was centrifuged to pellet the bacterial cells and the supernatant was measured by Cd atomic infrared absorbance.

Plastic degradation.

One $cm^2$ of polyethylene vinyl sheet was irradiated by UV radiation at 140 nm for 1 hour and incubated in trypticase soy broth with Strain SH2B at 64° C. for 2 days. Scanning electron microscopic analysis was performed on the vinyl surface of the treated samples.

RESULTS

Strains SH2A and SH2B were named *Bacillus midousuji* after the place at which the bacterial strains were found in composted leaves and branches.

1. Activity in Different Media

The results showed the strains to be gram-positive rods capable of spontaneous spore formation. SH2A produced acid from mannose, maltose, salicin, trehalose, sucrose, mannitol, fructose and raffinose. SH2A was also positive for indole production, nitrate reduction, β-glucosidase, β-glucuronidase, urease, and DNAase activity (Table I).

TABLE I

Characterization Of Activity Of Strains SH2A and SH2B

| Medium containing: | SH2A | SH2B |
|---|---|---|
| 1. Mannose | + | + |
| 2. Lactose | − | − |
| 3. Maltose | + | + |
| 4. Glycerol | − | − |
| 5. Salicin | + | + |
| 6. Voges Proskauel Reaction | − | − |
| 7. Trehalose | + | + |
| 8. Sucrose | + | + |
| 9. Mannitol | + | + |
| 10. Fructose | + | + |
| 11. Raffinose | + | − |
| 12. Nitrate Reduction | + | + |
| 13. β-glucosidase | + | + |
| 14. O-Nitrophenyl G β-galactosidase | − | − |
| 15. β-glucuronidase | + | + |
| 16. Arginine Dehydrogenase | − | − |
| 17. Urease | + | + |

SH2A is sensitive to both kanamycin at concentrations of 50 $\mu$g/ml and to ampicillin at concentrations of 50 $\mu$g/ml (Table II).

TABLE II

Bacterium Activity In Various Media

| Characteristics studied: | SH2A | SH2B |
|---|---|---|
| 1. Growth in trypticase soy agar containing 5% sheep's blood | + | + |
| 2. Hemolysis activity in trypticase soy agar containing 5% sheep's blood | − | − |
| 3. DNAse activity in agar containing DNA | + | + |
| 4. Growth in trypticase soy agar medium containing 7.5% NaCl | + | + |
| 5. Growth in Muller-Hinton agar containing 50 $\mu$g/ml kanamycin | + | + |
| 6. Growth in Muller-Hinton agar containing 50 $\mu$g/ml ampicillin | − | − |
| 7. Growth in n agar medium containing X-gal | − | − |

Strain SH2A displays a smooth colony surface on trypticase soy agar and produces a homogeneous suspension during growth in trypticase soy broth.

Another strain, SH2B, was positive for acid production from mannose, maltose, salicin, trehalose, sucrose, mannitol, fructose, and for indole production, nitrate reduction, β-glucosidase, β-glucuronidase, urease, and DNAase activity (Table I).

This strain is resistant to kanamycin at concentrations of 50 $\mu$g/ml, but sensitive to ampicillin at concentrations of 50 $\mu$g/ml (Table II).

Strain SH2B forms sticky colonies on trypticase soy agar and shows filamentous growth in trypticase soy broth.

Both SH2A and SH2B strains are thermophilic extremophiles and require at least 62° C. to grow.

Strains SH2A and SH2B grew in medium containing 7.5% NaCl. These strains do not reveal hemolytic activity in sheep blood agar plates (Table II).

Figure 1:
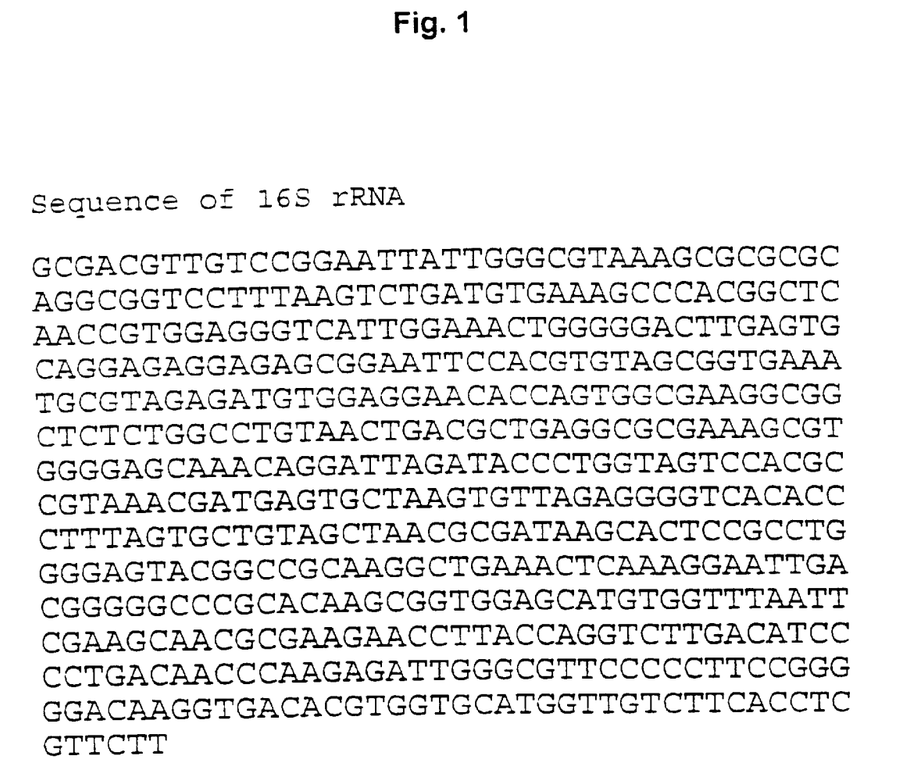
FIG. 1. Nucleic acid sequence of the bacterium strain SH2A and SH2B 16S rRNA.

Comparison of the sequences for the 16S rRNA genes with other bacterial rRNA genes indicated that both strains are new species in the genus Bacillus (FIG. 1).

2. Biodegradation of tuna fish head and extraction of DHA.

Tunafish heads containing 27% DHA were biodegraded by Strain SH2A. After 4 hour and 8 hour incubation periods, the free DHA concentration increased to 60%.

3. Biodegradation of PCB.

Twenty ppm of PCB was completely degraded by Strain SH2B after 5 days of incubation.

4. Bacterial accumulation of heavy metal (Cd).

Six $\mu$g of $Cd(NO_3)4H_2O$ in trypticase soy broth (2.2 ppm of Cd) containing $1 \times 10^7$ cells/ml of Strain SH2B was incubated at 64° C. for 3 days. After the incubation period, the sample was centrifuged and supernatant was analyzed. The supernatant contained 0.036 ppm of Cd concentration after 3 days of incubation (0.016 times dilution).

5. Plastic degradation.

A one $cm^2$ sample of polyethylene vinyl sheet was irradiated by UV radiation at 140 nm for 1 hour, and incubated in trypticase soy broth with Strain SH2B at 64° C. for 2 days. Scanning electron microscopic analysis showed evidence of biodegradation; the plastic surface contained holes. The control plastic surface (no UV irradiation) remained intact in the absence or presence of bacterial cells. Applicants speculate that the intact plastic is a polycarbohydrate film and that UV irradiation converted the film to a carboxylated film on which the bacterial cells could adhere, grow and cause degradation of the plastic.

Second Series Of Experiments

Bacterial Strains: Origin of the isolate.

Strains SH2A and Strain SH2B were isolated from a sample of compost collected in Osaka, Japan.

Culture methods and Media.

Regular aerobic techniques were used in all experiments. Strains SH2A and SH2B were cultured on trypticase soy medium (BBL) at 64° C.

Biodegradation of squid

One hundred kilogram of squid were mixed with a suspension of cells of Strain SH2A and incubated at 62° C., for 6 hours. The biodegraded samples were assayed for DHA, EPA and PCB and other features, such as fatty acid. Free fatty acid was obtained by n-hexane extraction. Analysis of DHA in the fatty samples was performed using gas liquid chromatography (GLC). Analysis of PCB was also performed using GLC.

RESULTS

The results of the degradation of squid using the bacterial strain SH2A after incubation at 65° C. for 6 hours incubation are shown in Table III.

TABLE III

Degradation of Squid

| FACTOR STUDIED | ACTIVITES OBSERVED |
| --- | --- |
| Fatty Acid | |
| DNA | 9.89% (Docosahexanoic acid) |
| EPA | 9.24 (EisocaPentanoic acid) |

TABLE III-continued

Degradation of Squid

| FACTOR STUDIED | ACTIVITES OBSERVED |
| --- | --- |
| Oxidation | 5.20 |
| Ionization | 132.87 |
| Per Oxidation | 0.20 |
| Color (APHA) | 85 |
| Heavy Metal | (atomic flame absorbance) |
| Cadmium | 0 |
| Zinc | 0 |
| Mercury | 0 |
| As | 0 |
| PCB | 0.13 (Gas chromatography) |

CONCLUSION

Biodegradation of tuna fish head and extraction of DHA.

Squid were biodegraded by Strain SH2A. After a 6 hour incubation period at 65° C., signs of degradation of the squid was observed.

Third Series Of Experiments:

Expansion of commercial activity arising from research in molecular and cellular biology, assures fermentation biotechnology of a bright future. In the long term, fermentation of renewable raw materials may replace depleting non-renewable fossil-fuels as a source of bulk chemicals.

Important recent developments in genetic engineering have extended the scope and potential of industrial fermentation technology. By using genetic engineering, one may construct new combinations of inheritable material by inserting the foreign genes into bacteria and other suitable organisms. One of the workhorses of the fermentation industry, Bacillus, may be a suitable bacterial host for such genetic engineering experiments.

In eukaryotic micro-organisms such as Saccharomyces and Aspergillus, protein synthesis and secretion systems are significantly more complex than in prokaryotes, e.g. Bacillus, particularly for producing recombinant non-pharmaceutical products, for example, enzymes.

Proteins and peptides, the translation products of structural genes, are the first obvious targets using recombinant DNA technology. In the future, it may be possible to manipulate primary and secondary metabolic systems to improve metabolite production by genetic engineering of key enzymes.

Thermophilic Bacillus producing high-temperature-stable enzymes, which have the ability to degrade substrates up to 100° C., have not only streamlined substrate-hydrolysis processes but have also created an impetus to isolate or construct other enzymes with highly stable properties.

Bacteria can express proteins at high levels. Gram-negative bacteria are in general not good extracellular protein secretors; gram-positive bacteria are significantly better at secreting extracellular proteins. Therefore, thermophilic Bacillus, such as SH2A and SH2B, may be a suitable producer of industrial enzymes.

Applicants will develop improvements of the bacterial strains SH2A and SH2B, possibly by DNA recombination, that will provide potent rapidly growing, but safe and effective recombinant bacteria that can be used for multiple purposes. For example, applicants plan to introduce genes which further enhances lipid, protein, carbohydrate, or fiber degradation. Lipids are an ideal target because the materials are easily collected from waste and requires only a minor handling process. The processed lipid can then be degraded in waste by bacterium.

Fourth Series Of Experiments:
The method of organic sludge dehydration by dehydration and freeze thaw processes using *Bacillus midousuji* Strains 1. General Concept of Sludge During removal suspended matters from waste water, there is a portion that precipitates and condenses at the separation stage, and that portion is referred to as sludge. Sludge comprises free matter, suspended matter, neutralization products, etc., and its concentration range from thousands of ppms to tens of thousands of ppms, and sizes of dispersed particles vary from colloids to coarse.

Sludge produced from water treatment process must be disposed as waste. In order to do so, it first must be dehydrated and have its mass reduced because it still has high water content even in its condensed state.

Characteristics of the sludge vary by particulates involved, additives such as condensing agents and products, and particle size distribution. Generally, dehydration process of sludge is difficult to execute, making sludge disposal a major problem.

2. Dehydration Methods

Sludge dehydration methods currently available include the following: drying bed method (easy to execute, but requires large tract of land), centrifuge method (applied mostly to raw sludge and digestive sludge), pressurized filtration method, and vacuum filtration method (used as vacuum filtration for this experiment).

3. Freeze/thaw Method

One major drawback of removing water content by adding condensing agents to the sludge and then dehydrating the sludge by above mentioned methods is that condensing agents increase the overall amount of sludge, and this goes against the intended purpose of dehydration which is to reduce mass, making such methods inappropriate.

One of the methods developed to solve this problem is the freeze/thaw method. This method, first used in Great Britain, showed that if sludge that is frozen at ideal conditions is thawed and then filtered, dehydration rates equal or greater than condensing agent addition method can be achieved.

4. Principle of Freeze/Thaw Treatment

Figure 2A:
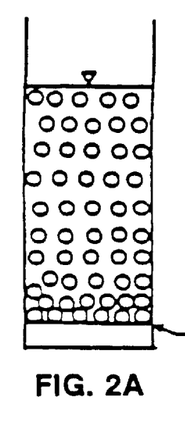
FIGS. 2A–2C. The theory of the dehydration effect described by Longsdon et al.
Figures 2B, 2C:
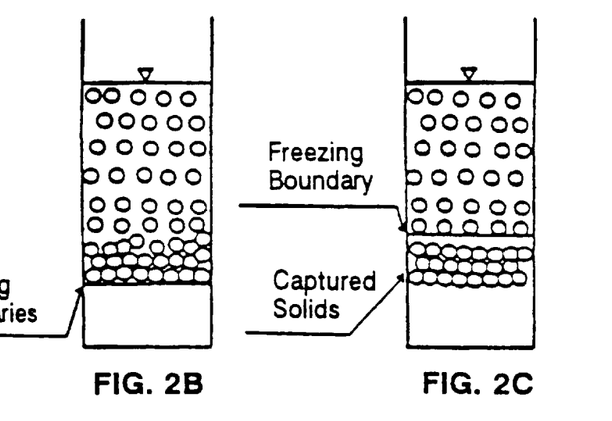

The goal of the Material Development by Freeze Thaw Treatment is to enlarge the particles, which reduces particle surface area, thereby reducing the amount of water adhering to the particle surface, as well as removing the water within the particles. The published reports discussing the theory behind this dehydration effect is few. G. S. Longsdon (U.S.) et al. describes the theory as in FIG. 2.

(1) In FIG. 2, the bottom of the container is designated as the cooling surface, and pure water first freezes from that cooling surface. With the enough water movement for the ice to form, sludge solids are condensed on the surface of the freezing surface in layers, not mixing with the forming ice.

(2) Water between the sludge particles as well as water adhering to the surface in contact with the freezing boundary is drawn to the ice by capillary force during this freezing process. Because of the resistance from the dehydrated solid layers, water movement slow down, and the solid layers collected is captured by the ice.

(3) Growth of the freezing boundary continues into the areas where water is moving freely, and the above mentioned process continues.

5. Characteristics of the Freeze/Thaw Treatment

For characteristics of the freeze/thaw treatment the following can be stated:

a. Dehydration treatment can be done without usage of chemicals, therefore:

i. Amount of sludge to be disposed in the final stage does not increase ii. There are no risks of secondary pollution from additives (when lime, which is used as filtration helpers, enters the ground, the soil becomes alkaline, preventing any plant growth).

b. Final product does not return to its original state even if water is added back in (this becomes vital during landfilling).

c. Filtration fluid remains clean even after use (in water treatment plants, depending on the circumstances, it may be reused as source water).

d. Compared to incineration and drying:

I. Sludge can be treated below normal temperature, so there are no risks of secondary pollution such as smoke and odor.

ii. Problems of materials and corrosion can be minimized.

iii. Energy consumption for the dehydration process is small.

iv. Maintenance procedures are simple, thereby reducing staff expense. The process can be fully automated.

6. Limitations of Freeze/Thaw Fusion Treatment

Sludge can mainly be divided into the following: organic sludge (sewage from domestic waste water), inorganic sludge (chrome, acidic detergent waste water and sludge from water treatment facilitates), and combination of the two. For organic sludge, in terms of achievable water load levels, dehydration effects are not as extensive as inorganic sludge. Currently, freeze/thaw treatment has been put into practice for inorganic sludge, but for this treatment method, the limit of organic content level treatable is 50%, making it inappropriate for sewage treatment. This is because the organic content level in the sewage is higher than the inorganic content level, making combined water removal difficult.

7. Degradation of Microorganisms

The purpose of this experiment is to improve the effect of freeze/thaw treatment for organic sludge, and by degrading microorganisms at high temperatures, we have attempted to remove combined water from the sludge. Also, we have studied the effect of surfactants and culture dissolving enzymes by adding them into the mix.

I. MATERIAL AND EQUIPMENT

1. Thermophilic bacteria

*Bacillus midousuji* ATCC5926 SH2A, SH2B

2. Saponin

Detergent made from amazone plant.

3. Enzyme

From *Achromobacter litycus* (Pure Chemical Inc.)

4. Sludge

Condensed inorganic sludge from water treatment facility, organic sludge sewage treatment facility, and standard activated sludge (incubated in a pH 7 medium containing glucose, pepton, potassium phosphate). Sludge used in the experiment were precipitated and condensed.

5. Sludge Freezing System

2×25×25 cm stainless container was used as sludge freezing container. Freezing of sludge was done by directly submerging them in a low constant temperature (ADVANTEC INC.) basin that can be adjusted to −40 degrees Celsius by antifreeze cooling.

6. Nutch apparatus

Dehydration of sludge was performed by Nutch apparatus under sewage testing methods.

7. Infrared Water Content Measure

This device measures water content and solids content by drying the sample with infrared beams, and measuring change in mass from water evaporation that result from that process (Kett Inc. FD-240). This process, called the dry mass reduction method, is one of the most basic measuring principles, and it is adopted as official standard measuring method in many organizations.

II. EXPERIMENTAL METHOD

1. Freeze/Thaw Method

Sludge from water treatment plants (inorganic sludge), sludge from sewage treatment plants (organic) that underwent microorganism degradation, and standard sludge were placed into sludge freezing containers. The freezing containers were then placed in the low constant temperature basins, and there sludge samples were frozen at $-10°$ C. for 3 hours. Later, sludge samples were thawed out by hot water.

2. Microorganism Degradation Method

Organic sludge samples were placed in a 50 ml container with a lid. Sludge samples were inoculated *B. midorisuji* and then incubated at 62° C. for 16 to 18 hours. Microorganism degradation was then executed.

3. Saponin Treatment

For organic sludge, 0.2 ml of saponin was added to every 20 ml of sludge.

4. Enzyme Treatment

For organic sludge, 0.01 g of enzyme was added to every 40 ml of sludge and then held at 37° C. for 18 hours. By combining methods and treatments of 1 through 4 mentioned above, water content levels and filtration velocity were measured. Measurements for water content and filtration velocity were executed as stated below:

(1) Measurement of Filtration Velocity

Sludge samples were placed into the Nutch apparatus. Amounts of filtration fluid were measured with progression of time during depressurization process. From the angles shown on resulting graphs, filtration velocity were calculated.

(2) Measurement of Sludge Water Content

After the sludge samples were filtered by treatment methods stated above, water content levels were measured by infrared moisture measure.

5. Measurement of burnt out

In order to determine the organic content levels of each sludge, burnt out process was performed.

a. Measurement of Water Content and Filtration Velocity for Inorganic Sludge

1. An unaltered sample was placed on the sample plate of the infrared water content measure and the water content of the source was measured.
2. (Depressurized Filtration) 15 ml samples were placed in the Buchonar's filtration of the device as in the diagram, and depressurized filtration as well as the stop watch were started. The times filtrated fluids took to deposit in the test tube inside the absorbance bottle were recorded (for the purpose of filtration velocity calculation). In case of pressurized filtration, additional filtration paper was placed on top of the samples, then beakers containing 200 ml were placed over the samples as weights and then adsorbs began.
3. Water content of the sludge on the filtration paper was measured by infrared water content measure.
4. (Freeze/Thaw) Samples were placed into the freeze containers, and the containers was placed in the low constant temperature basins. The samples were frozen there by 3 hours of cooling (freezing temperature at $-3°$ C., then fused with hot water.
5. After the samples that were frozen and fused went through adsorbed filtration, water content levels were measured.

b. Measurement of Water Content and Filtration Velocity for Organic Sludge

1. As with the organic sludge, water content levels of the source sludge were measured.
2. For organic sludge, water content levels were measured for each of the following: freeze/thaw without treatment before vacuum depressurized filtration, microorganisms degraded only, microorganisms degraded after frozen/thaw, frozen/thaw after microorganisms degraded, saponin treatment, and frozen/thaw after saponin treatment. Saponin treatment is done as follows:

1) microorganisms degradation: sludge samples were taken into tubes, and microorganisms were inoculated to them. Microorganisms were incubated in incubators at 62° for 16 to 18 hours.

2) Saponin treatment: For every 20 ml sample, 0.2 ml of saponin was added.

3) Standard activated sludge samples went through the same process as the organic sludge, with 0.01 g of enzyme added and held at 37°, and after freeze/thaw and ads or bed filtration, water content was measured.

4) Mass Reduction by Burnt Out

Approximately 15 ml of the samples were filtered, and dehydrated cakes on top of filtration paper were dried in a dryer. These became the evaporation residues (g). These were burnt out in a platinum pot, and the mass of the burnt residue, and the ratio of mass decrease of evaporated residue by burnt (%) were calculated.

Figure 3A:
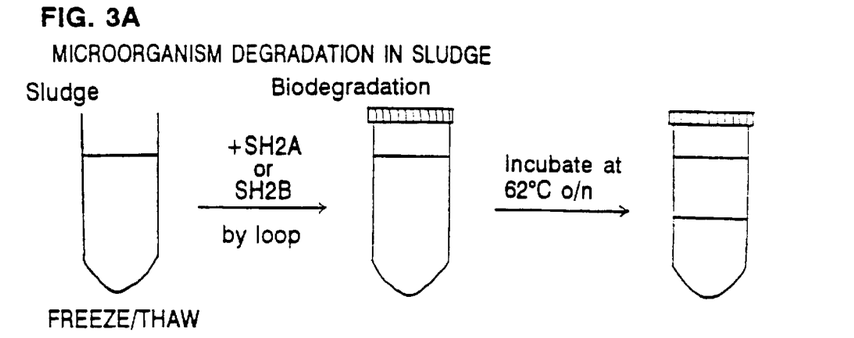
FIGS. 3A–3B. Microorganism Degradation in Sludge.
Figure 3B:
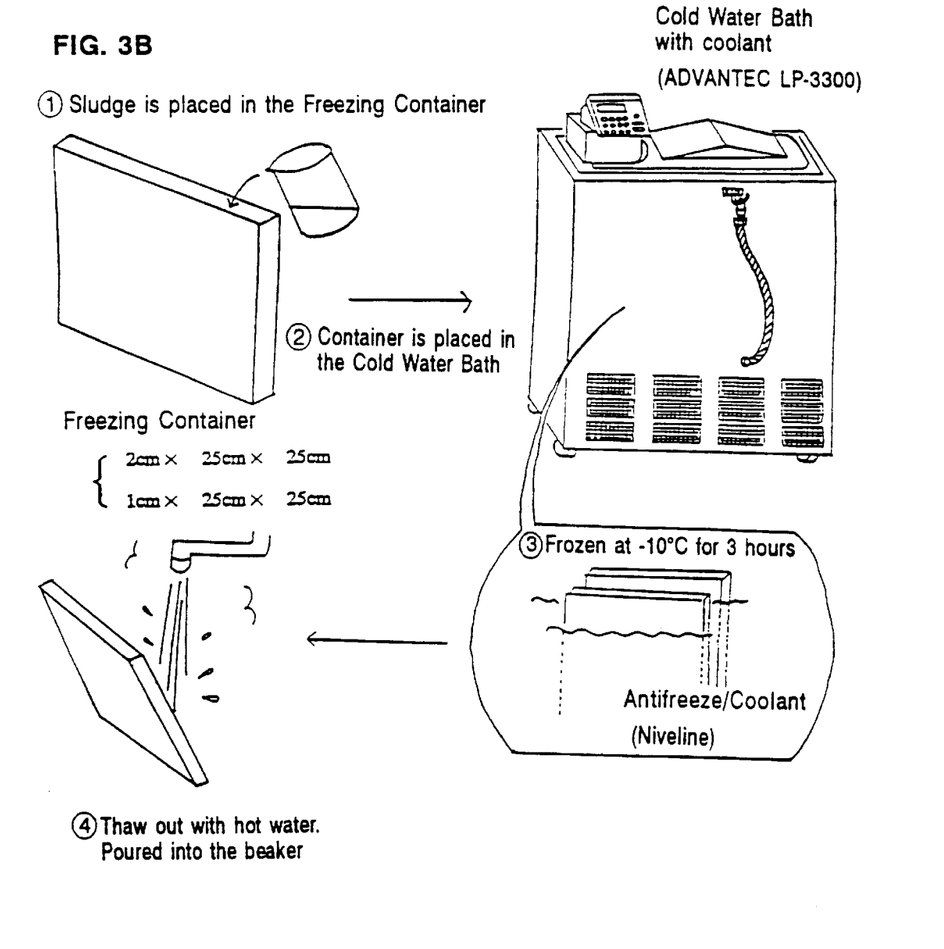

FIG. 3 describes Microorganism Degradation in sludge. The Sludge is placed in the Freezing Container. The Container is placed in a cold water bath. The Sludge is frozen at $-10°$ C. for 3 hours. Then, it is thaw out with hot water and poured into a beaker.

Figure 4A:
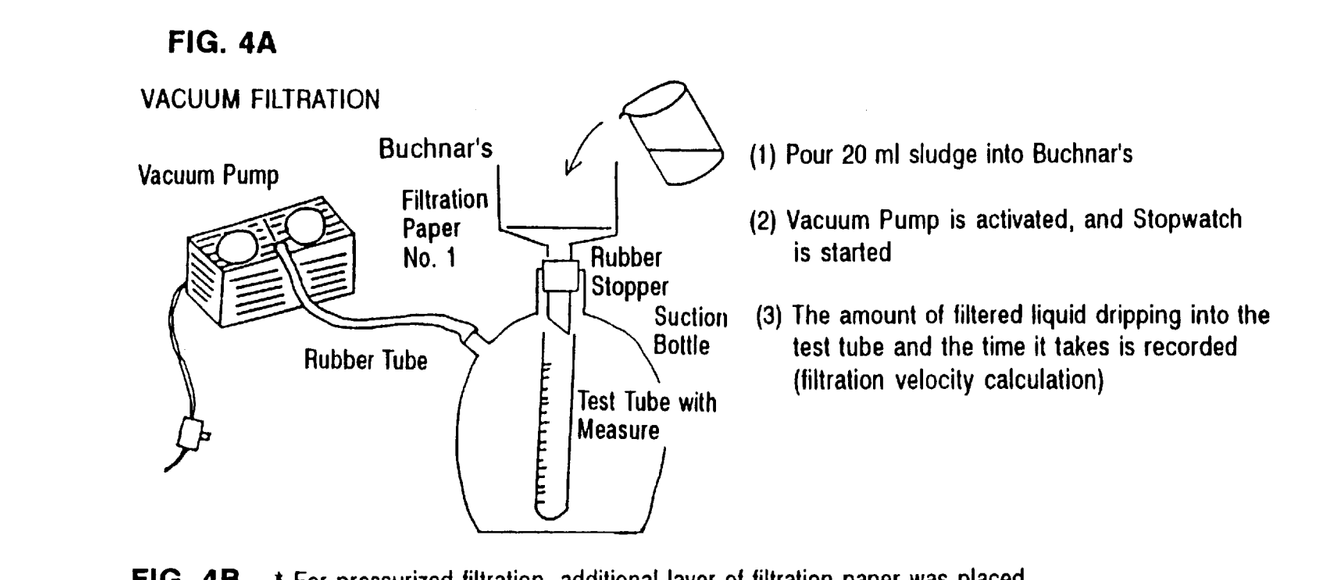
FIGS. 4A–4B. Vacuum Filtration.
Figure 4B:
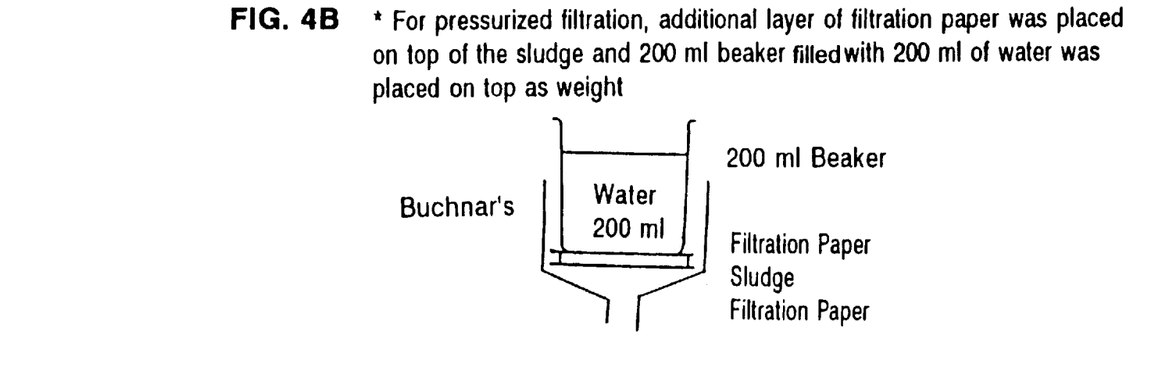
Figure 5:
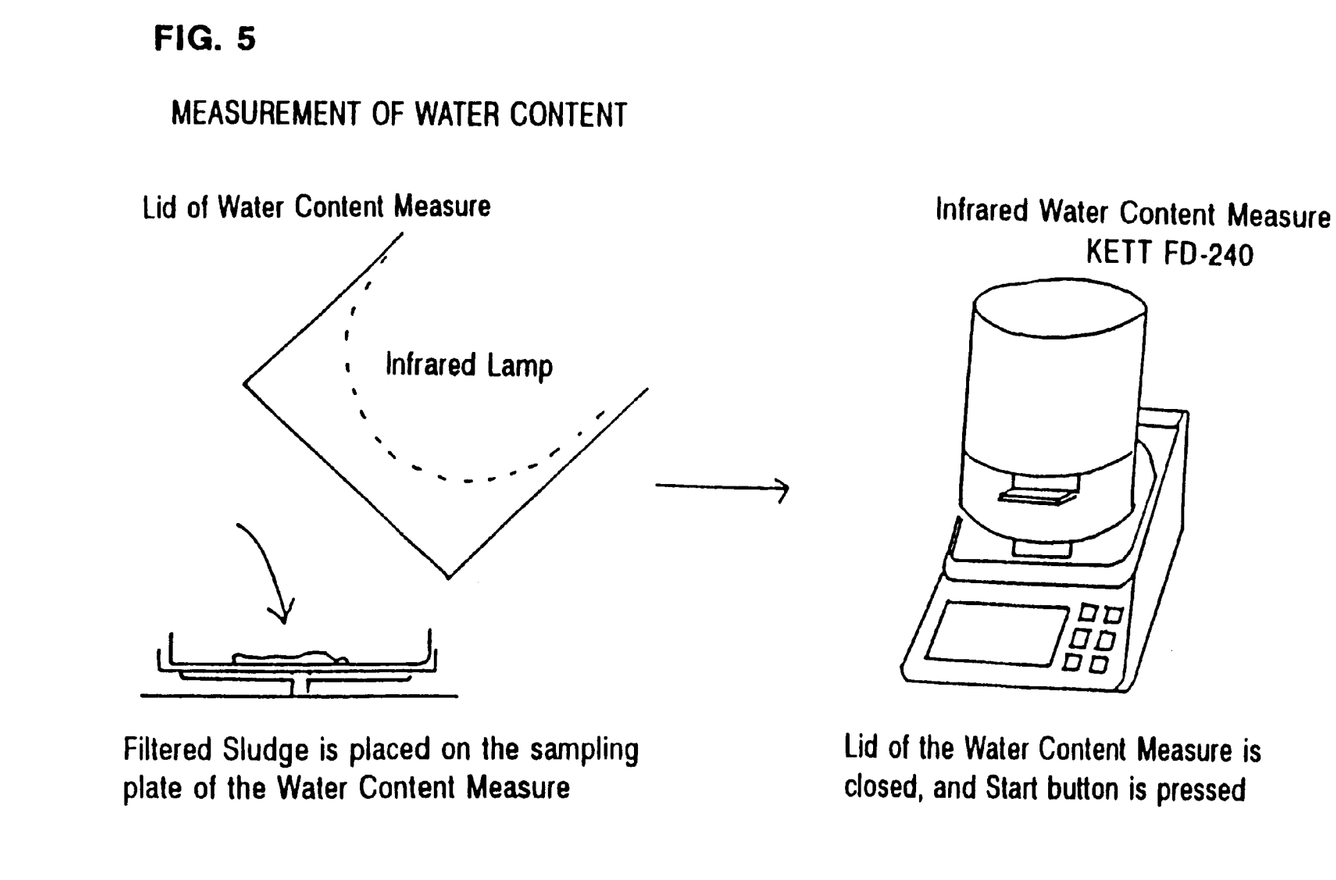
FIG. 5. Measurement of Water Content.

FIG. 4 describes the steps of Vacuum Filtration. 20 mls of sludge is poured into Buchnar's Filtration Paper No.1. Vacuum pump is activated and stopwatch is started. The amount of filtered liquid dripping into the test tube and the time it takes is recorded (filtration velocity Calculation) For pressurized filtration, additional layer of filtration paper was placed on top of the sludge and 200 ml beaker filled with 200 ml of water was placed on top as a weight. The measurement of water content is as described in FIG. 5. The filtered Sludge is placed on the sampling plate of the Water Content Measure. Lid of the Water Content Measure is closed and start button is pressed.

III. EXPERIMENTAL RESULTS

1. Sludge from Water Treatment Sludge (Inorganic Sludge)

The water content levels of the source sludge were, in all water treatment facilities, around 95%. In contrast, sludge samples that went through vacuum filtration only had an average of 79%, sludge that went through freeze/thaw and vacuum filtration had an average of 63%. Also, pressurized filtration lowered water content levels by 7% when compared the vacuum filtration (Water Treatment Facility K).

When freeze/thaw was performed, compared to vacuum filtration only, filtration velocity increased drastically, with Water Treatment Facility Y at 6.8 times greater, Water Treatment Facility at 2.8 times greater, and Water Treatment Facility K at 8.8 times greater.

2. Sludge from Sewage Treatment Facility (Natural Organic Sludge)

The water content of the source sludge was at 98%. This was lowered to 83.7% after vacuum filtration. After the source sludge went through microorganism degradation, water content level dropped to 77.4% for SH2A strain, and 74.3% for SH2B strain. For sludge that went through microorganism degradation after freeze/thaw (SH2A only), water content level dropped to 73.5%. On the other hand, for sludge samples that went through freeze/thaw after microorganism degradation, water content levels were 74.6% for SH2A, and 76.3% for SH2B.

Filtration velocity for the sludge that went through freeze/thaw was 1.7 times greater than those that received no treatment, while sludge samples that went through microorganism degradation was 1.5 times greater for SH2A, and 1.3 times greater for SH2B than those that received no treatment. For sludge that went through microorganism degradation after freeze/thawing, filtration velocity was the same as those that received no treatment. But for sludge samples that went through freeze/thaw after microorganism degradation, filtration velocity were 3.3 times greater for SH2A, and 3.0 times greater for SH2B than those that received no treatment.

For sludge with saponin added, water content was 84.1% for those that received saponin treatment only, and the filtration remained the same as untreated sludge. When freeze/thaw treatment is performed on this sludge, water content decreased to 80.3% and filtration velocity increased by 20%. If microorganism treatment (SH2A) was performed on top of that, water content dropped to 74.6%, and filtration rate increased by 10%.

When enzymes were added, water content level dropped to 78.4%, with filtration rate 10% higher.

3. Standard Activated Sludge

The water content of the source sludge was 99.4%. After vacuum filtration, it dropped to 84.8%, and after freeze/thaw it dropped to 80.6%. For sludge samples that only went through microorganism degradation, water content levels were 90.1% for SH2A, and 88.2% for SH2B. For sludge that went through microorganism degradation after freeze/thaw, water content was 73.8% for SH2B. For sludge samples that went through freeze/thaw after microorganism degradation, water content levels were 77.3% for SH2A, and 78.1 for SH2B.

For sludge that only went through freeze/thaw, filtration velocity was 1.5 times greater than those that received no treatment. For sludge samples that only went through microorganism degradation, filtration velocity for both SH2A and SH2B were 0.5 times greater than those that received no treatment. For sludge that went through microorganism degradation after freeze/thaw (SH2B), filtration velocity was 2.8 times greater than those that received no treatment. For sludge samples that went through freeze/thaw after microorganism degradation, filtration velocity were 2.4 times greater for SH2A, an 2.6 times greater for SH2B than those that received no treatment.

For sludge with saponin added, those with saponin added only had water content of 79.0%, with filtration velocity 1.5 times greater. When freeze/thaw was done after saponin ersctinent, water content decreased to 78.3%, with filtration velocity 2.4 times greater.

For sludge with enzymes added, those with enzymes added only had water content of 84.2%, with filtration velocity 0.9 times greater. When freeze/thaw was done after enzyme addition, water content decreased to 81%, with filtration rate 2.7 times greater.

4. Mass reduction by burnt out

For water treatment facility sludge, ratio of mass decrease to suspended matter was 29.8% for Treatment Facility Y, 23.0% for Treatment Facility K, 41.6% for Treatment Facility K. For natural organic sludge, the ratio was 76.6%.

TABLE 1

Water Content Variation due to Treatment Methods (Inorganic Sludge)

| | Prefiltration Treatment | Average Water Content | Notes |
|---|---|---|---|
| Sludge from Water Treatment Facility Y | None | 81.4 (n = 3) | |
| | Freeze/Thaw | 61.4 (n = 3) | Frozen at −3° C. |
| Sludge from Water Treatment Facility M | None | 72.7 (n = 3) | |
| | Freeze/Thaw | 62.1 (n = 2) | Frozen at −3° C. |
| Sludge from Water Treatment Facility K | None | 82.6 (n = 2) | |
| | Freeze/Thaw | 65.2 (n = 2) | Frozen at −3° C. |

TABLE 2

Filtration Velocity Variation due to Treatment Methods (Inorganic Sludge)

| | Prefiltration Treatment | Average Water Content | Notes |
|---|---|---|---|
| Sludge from Water Treatment Facility Y | None | 149.1 (n = 3) | |
| | Freeze/Thaw | 1016 (n = 3) | Frozen at −3° C. |
| Sludge from Water Treatment Facility M | None | 288.9 (n = 3) | |
| | Freeze/Thaw | 798.5 (n = 2) | Frozen at −3° C. |
| Sludge from Water Treatment Facility K | None | 105.5 (n = 2) | |
| | Freeze/Thaw | 923.3 (n = 2) | Frozen at −3° C. |

TABLE 3

Water Content Variation due to Treatment Methods (Natural Organic Sludge)

| Prefiltration Treatment | Average Water Content | Standard Deviation | Notes |
|---|---|---|---|
| None | 83.7 (n = 4) | 0.723 | |
| Freeze/Fusion | 74.8 (n = 3) | 0.54 | |
| Microorganism Degradation | | | |
| SH2A | 77.4 (n = 2) | | |
| SH2B | 74.3 (n = 1) | | |
| Freeze/Fusion Microorganism Degradation | | | |
| Control | 74.8 (n = 2) | | |
| SH2B | 73.5 (n = 8) | 0.48 | 65° C., 6–12 h |
| Microorganism Degradation & Freeze/Thaw | | | |
| SH2A | 74.6 (n = 6) | 0.56 | |
| SH2B | 76.3 (n = 2) | | |
| Saponin Treatment | 84.1 (n = 2) | | |
| Saponin Treatment + Freeze/Thaw | 80.3 (n = 3) | | |
| Enzyme Treatment | 74.6 (n = 2) | | |
| Enzyme Treatment + Freeze/Thaw | 78.4 (n = 4) | 0.97 | 65° C., 8 h |

TABLE 4

Filtration Velocity Variation due to Treatment Methods
(Natural Organic Sludge)

| Prefiltration Treatment | Average Filtration Velocity | Standard Deviation | Notes |
|---|---|---|---|
| None | 365 (n = 4) | 41.3 | |
| Freeze/Thaw Microorganism Degradation | 629 (n = 4) | | |
| SH2A | 568 (n = 3) | | |
| SH2B | 496 (n = 4) | | |
| Freeze/Fusion Microorganism Degradation | | | |
| Control | 325 (n = 2) | | |
| SH2B Microorganism Degradation & Freeze/Thaw | 376 (n = 3) | 40 | 65° C. 6–12 h |
| SH2A | 1230 (n = 3) | 111 | |
| SH2B | 1173 (n = 1) | | |
| Saponin Treatment | 359 (n = 2) | | |
| Saponin Treatment + Freeze/Thaw | 472 (n = 3) | | |
| Enzyme Treatment | 408 (n = 1) | | |
| Enzyme Treatment + Freeze/Thaw | 404 (n = 4) | 18.6 | |

TABLE 5

Water Content Variation due to Treatment Methods
(Standard Activated Sludge)

| Prefiltration Treatment | Average Water Content | Standard Deviation | Notes |
|---|---|---|---|
| None | 84.8 (n = 4) | 0.54 | |
| Freeze/Thaw Microorganism Degradation | 80.6 (n = 3) | 1.65 | |
| SH2A | 90.1 (n = 3) | 1.21 | |
| SH2B | 88.2 (n = 4) | 1.81 | |
| Microorganism Degradation & Freeze/Thaw | | | |
| SH2A | 77.3 (n = 2) | 1.02 | |
| SH2B | 78.1 (n = 3) | 1.83 | |
| Saponin Treatment | 79 (n = 3) | | |
| Saponin Treatment + Freeze/Thaw | 78.3 (n = 1) | | |
| Enzyme Treatment | 84.2 (n = 3) | 0.69 | |
| Enzyme Treatment + Freeze/Thaw | 81 (n = 1) | | |

TABLE 6

Filtration Velocity Variation due to Treatment Methods
(Standard Activated Sludge)

| Prefiltration Treatment | Average Filtration Velocity | Standard Deviation | Notes |
|---|---|---|---|
| None | 821 (n = 4) | 72.7 | |
| Freeze/Thaw Microorganism Degradation | 1256 (n = 4) | 120 | |
| SH2A | 392 (n = 3) | 52.3 | |
| SH2B | 431 (n = 4) | 53 | |
| Microorganism Degradation + Freeze/Thaw | | | |
| SH2A | 1996 (n = 2) | | |
| SH2B | 2111 (n = 3) | 442 | |
| Saponin Treatment | 1212 (n = 3) | 48 | |
| Saponin Treatment + Freeze/Thaw | 1961 (n = 1) | | |
| Enzyme Treatment | 736 (n = 3) | 91.2 | |
| Enzyme Treatment + Freeze/Thaw | 2236 (n = 1) | | |

TABLE 7

Mass Reduction by Burnt Out

| | Water Treatment Facility Y | Water Treatment Facility M | Water Treatment Facility K | Organic Sludge |
|---|---|---|---|---|
| Sample (g) | 12.7245 | 14.83 | 13.5359 | 14.1555 |
| Evaporation Residue (g) | 0.6632 | 0.5205 | 1.1722 | 0.2143 |
| burnt out Residue (g) | 0.4657 | 0.4008 | 0.685 | 0.0502 |
| Mass Reduction by Burnt out (g) | 0.1975 | 0.1197 | 0.4872 | 0.1641 |
| Ratio of Mass Reuction to Evaporation Residue (%) | 29.8 | 23 | 41.6 | 76.6 |

IV. DISCUSSIONS

For inorganic sludge, freeze/thaw has become a practical and viable method of dehydration, as stated in the Preface. From the experimental results, we were able to obtain more than adequate amounts of reproduction data.

From the performance of mass reduction by burnt out, we can see that organic content levels on inorganic sludge and natural organic sludge vary greatly, and as said in the past, freeze/thaw was more effective in dehydration for inorganic sludge than organic sludge.

In case of natural organic sludge, we were able to obtain the same level as the sludge that went through freeze/thaw with microorganism degradation alone. Filtration rates were slightly greater than untreated sludge, therefore it has been proven that microorganism degradation is effective for natural organic sludge. On the other hand, combining freeze/thaw with microorganism degradation brought no greater decrease in water content levels, thus we saw no merit of microorganism degradation in this case.

But the point of interest was the filtration rates. Among the two types of combination, microorganism degradation done first and then freeze/thaw done later increased the filtration velocity by 3 times compared to untreated sludge. This fact may open new opportunities for microorganism degradation.

For standard activated sludge, microorganism degradation alone brought no visible effect in water content or filtration velocity. The fact that sludge that went through degradation became thicker in quality than the sludge before the degradation treatment was plainly visible to the naked eye, and this observation was backed by data that showed decrease in filtration velocity.

But, by combining it with freeze/thaw, water content levels decreased and filtration velocity increased, compared to sludge that undergone freeze/thaw only. If the data for the two treatment methods combined are accurate, and if these superior data results are not due to separate measurement dates nor due to errors in the execution of the experiment, combined effects of the two treatment methods may open many new opportunities.

From the experimental results, the question of which method should be done first arises. For natural organic sludge, order did not matter in terms of water content levels, but almost all other data showed that microorganism degradation should be done first. Since we have no microscopic data, mechanisms of how microorganism degradation work in the sludge remain unclear, but it is suspected that the sludge is either degraded or damaged by the microorganism, which in turn increase the effectiveness of the freeze/thaw. When freeze/thaw is performed first, it is suspected that the microorganism degradation performed afterwards increase the microorganisms within the sludge, eliminating the effect of the freeze/thaw treatment.

As for saponin treatment and enzyme treatment, saponin treatment is effective in standard activated sludge, whereas enzyme treatment is effective in natural organic sludge. It seems that combining these two types of method with freeze/thaw may bring about a new method of sludge treatment, but this portion of the experiment was done as a supplement, and resulting data are too incomplete for further comment.

Figure 6:
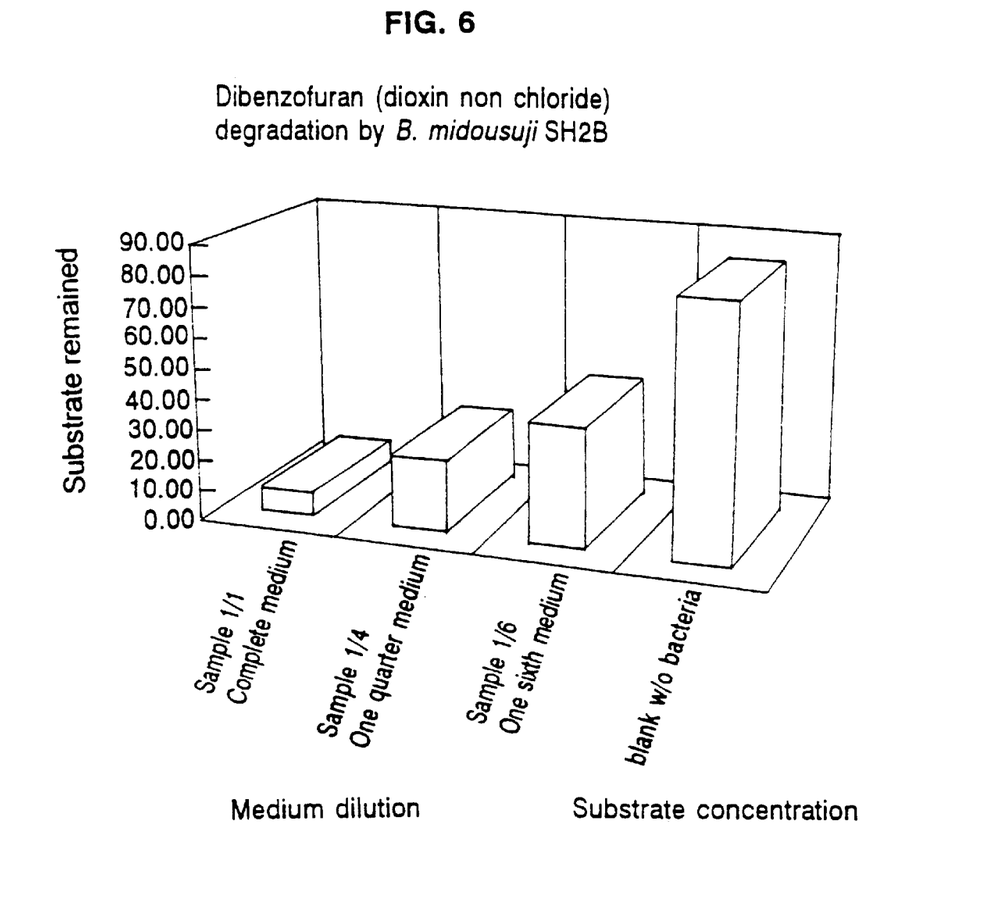
FIG. 6. Dibenzofuran (dioxin non chloride) Degradation by *B. midousuji* SH2B.
Figure 7:
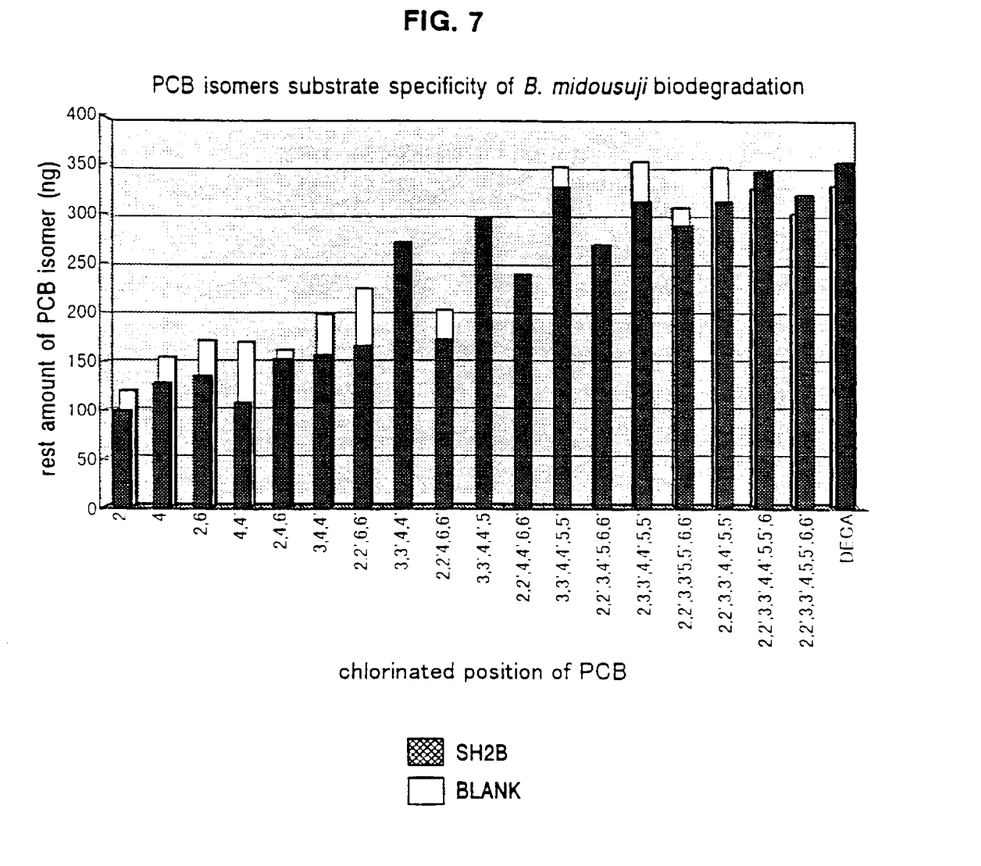
FIG. 7. PCB Isomers Substrate Specificity of *B. midousuji* Biodegradation.

Fifth Series Of Experiments:
Biodegradation of Dibenzofuran by *Bacillus midousuji* ATCC 202050 SH2B
1. Materials and Methods
    1) Dissolve dibenzofuran (Kanto Chemical Co., Ltd, Tokyo) in n Hexan at 10,000 ppm.
    2) Dilute DF in Tripticase Soy Broth (BBL) at 100 ppm up to 1 ml, medium was also diluted to 1×, ¼×, ⅙× by distilled water.
    3) Inoculate SH2B strain to DF solution (0.5 mL) at $10^5$ cells.
    4) Incubate DF w/SH2B at 64 degree C 42 h with shaking bath.
2. Detection of DF remained in solution
    1) Add internal control ($^{37}Cl$ Tetra Cl-DF 10 ng) to each sample tube.
    2) Add HCL up to 2N in solution.
    3) Put the tube 1 hour and add 3 mL PW up to 3.55 mL.
    4) Extract DF by toluene, 3 times.
    5) Extract by N2 gas up to 100 nL.
    6) Detect DF by GC-MS(Gas Chromatography-Mass Spectrometry) and quantitate DF by SIM(Single Ion Monitoring) system.
    7) Metabolite was also detected by GC-MS with TIM system.
3. Results with FIG. 6
    Blank: 90 ug of DF
    Complete medium: 10 ug of DF
    ¼ medium: 30 ug of DF
    ⅙ medium: 45 ug of DF
    No metabolite was detected, may be degraded to H2O.
4. Comments
    Thermophile *Bacillus midousuji* ATCC202050, SH2B strain degraded one of the dioxin, non-chloridedibenzofuran to carbon dioxide and water.

Sixth Series Of Experiments:

Biodegradation of PCB isomers

1)Wash three glass flasks with Teflon screwed cap three times by ethanol and dry them up.

2)Pour 40 ml broth (Tripticas soy broth-BBL) into the flask.

3)Dispose 30 µl PCB in ethanol by Hamilton micro-sylinge.

4)Isolate SH2A, SH2B, ($10^6$ cfu) and broth as a negative control) respectively into the flask. Isolate for 60 hours at 62° C.

5)Decant each content into the glass transport bottle respectively. The rest was washed out by saline and transfer to the transport bottle without dead space.

6)Total PCB in the transport bottle was extracted by toluene and quantified by gas-mas spectrometry.

RESULTS

1)Thermophilic bacterium *Bacillus midousuji* ATCC 55926 SH2B strain degraded PCB isomers such as chlorinated hiphenyl (1)2, (2)4, (3)2.6, (4)4.4, (5)3.4.4, (6)2.2, 6.6, (7)2.2, 4.6.6

Substrate specificity of PCB isomers by *B. midosuji*

| PCB isomers by chlorinated position | (1) PCB amount remained after digestion by SG2b (ng) | Blank (ng) | (2) rating of (1)/(2) (%) |
|---|---|---|---|
| 1 1 | 99.3 | 118.6 | 0.837 |
| 2 4 | 127.5 | 153.4 | 0.831 |
| 3 2, 6 | 135.0 | 170.8 | 0.790 |
| 4 2, 4, 6 | 152.1 | 161.2 | 0.994 |
| 5 4, 4 | 107.6 | 169.0 | 0.637 |
| 6 2, 2' 6, 6' | 165.9 | 224.4 | 0.739 |
| 7 2, 2' 4, 6, 6' | 172.4 | 202.8 | 0.850 |
| 8 3, 4, 4' | 156.6 | 198.4 | 0.789 |
| 9 2, 2', 4, 4', 6, 6' | 239.1 | 216.4 | 1.105 |
| 10 3, 3' 4, 4' | 271.0 | 200.3 | 1.353 |
| 11 2, 2', 3, 4', 5, 6, 6' | 269.2 | 269.6 | 0.999 |
| 12 3, 3', 4, 4', 5 | 296.2 | 234.2 | 1.265 |
| 13 2, 2', 3, 3', 5, 5', 6, 6' | 288.4 | 308.4 | 0.935 |
| CO2 and | | | |
| 14 3, 3', 4, 4' 5, 5' | 327.6 | 350.4 | 0.935 |
| 15 2 ,3, 3', 4, 4', 5, 5' | 312.5 | 355.5 | 0.879 |
| 16 2, 2', 3, 3', 4, 5, 5', 6, 6' | 320.0 | 302.5 | 1.058 |
| 17 2, 2', 3, 3', 4, 4', 5, 5' | 312.9 | 350.1 | 0.894 |
| 18 2, 2', 3, 3', 4, 4', 5, 5', 6 | 343.8 | 328.4 | 1.047 |
| 19 Deca | 353.2 | 331.4 | 1.066 |

---

What is claimed is:

1. A method of degrading an organic material contained in a sludge which comprises treating the sludge with an effective, degrading amount of a microorganism selected from the group consisting of a microorganism strain SH2A ATCC Accession No. 55926 microorganism strain SH2B ATCC Accession No. 202050 and mutants derived therefrom which retain the degrading activity thereof, so as to thereby degrade the material in the sludge.

2. The method of claim 1, wherein the organic material is a plastic material.

3. The method of claim 2, wherein the plastic material is polyethylene.

4. The method of claim 3, wherein the polyethylene is irradiated prior to treatment with the microorganism.

5. The method of claim 4, wherein the irradiation comprises exposing the polyethylene to ultra-violet light.

6. The method of claim 1, wherein the organic material is a Dioxin or a polychlorobiphenyl.

7. The method of claim 6, wherein the Dioxin is dibenzofuran.

8. The method of claim 1, wherein the treatment is effected at a temperature from about 62° C. to about 100° C.

9. The method of claim 8, wherein the temperature is about 62° C.

10. The method of claim 1, wherein the treatment is effected at a pH at about 5.0 to about 8.0.

11. The method of claim 10, wherein the pH is about 7.4.

12. The method of claim 1, wherein the treatment is effected in an aerobic environment.

* * * * *